US006530876B1

(12) United States Patent
Spence

(10) Patent No.: US 6,530,876 B1
(45) Date of Patent: Mar. 11, 2003

(54) SUPPLEMENTAL HEART PUMP METHODS AND SYSTEMS FOR SUPPLEMENTING BLOOD THROUGH THE HEART

(76) Inventor: Paul A. Spence, 5818 Orion Rd., Louisville, KY (US) 40222

( * ) Notice: Subject to any disclaimer, the term of this patent is extended or adjusted under 35 U.S.C. 154(b) by 0 days.

(21) Appl. No.: 09/557,562

(22) Filed: Apr. 25, 2000

(51) Int. Cl.⁷ .............................................. A61N 1/362
(52) U.S. Cl. ...................................................... 600/16
(58) Field of Search ............ 600/16–18; 604/4.01–6.16, 604/8–10

(56) References Cited

U.S. PATENT DOCUMENTS

| | | | |
|---|---|---|---|
| 2,935,068 A | 5/1960 | Donaldson | 128/348 |
| 3,195,540 A | 7/1965 | Waller | 128/422 |
| 3,942,535 A | 3/1976 | Schulman | 128/419 |
| 4,790,825 A | 12/1988 | Bernstein et al. | 604/170 |
| 4,995,857 A | 2/1991 | Arnold | 600/16 |
| 5,171,218 A | 12/1992 | Fonger et al. | 604/164 |
| 5,190,528 A | 3/1993 | Fonger et al. | 604/171 |
| 5,290,227 A | 3/1994 | Pasque | 600/16 |
| 5,344,443 A | 9/1994 | Palma et al. | 623/3 |
| 5,545,191 A | 8/1996 | Mann et al. | 607/57 |
| 5,695,471 A | 12/1997 | Wampler | 604/131 |
| 5,704,891 A | 1/1998 | Mussivand | 600/16 |
| 5,711,753 A | 1/1998 | Pacella et al. | 600/16 |
| 5,738,649 A | 4/1998 | Macoviak | 604/43 |
| 5,741,316 A | 4/1998 | Chen et al. | 607/61 |
| 5,743,845 A | 4/1998 | Runge | 600/16 |
| 5,840,070 A | 11/1998 | Wampler | 604/131 |
| 5,858,009 A | 1/1999 | Jonkman | 604/264 |
| 5,924,848 A | 7/1999 | Izraelev | 417/420 |
| 5,924,975 A * | 7/1999 | Goldowsky | |
| 5,938,412 A | 8/1999 | Izraelev | 417/423.7 |
| 5,941,813 A | 8/1999 | Sievers et al. | 600/16 |
| 5,947,892 A | 9/1999 | Benkowski et al. | 600/16 |
| 5,948,006 A | 9/1999 | Mann | 607/61 |
| 5,965,089 A | 10/1999 | Jarvik et al. | 422/44 |
| 6,299,575 B1 * | 10/2001 | Bulling | |

FOREIGN PATENT DOCUMENTS

| | | |
|---|---|---|
| WO | WO 97/42413 | 11/1997 |
| WO | WO 99/59652 | 11/1999 |

OTHER PUBLICATIONS

R.J. Baird, M.D. et al., *Survey of Mechanical Assistance of the Circulation and the Present Status of Left–Heart Bypass*, Article, 1965.
World Heart Corporation, *World Heart*, 1998 Annual Report.

* cited by examiner

*Primary Examiner*—Mark Bockelman
(74) *Attorney, Agent, or Firm*—Wood, Herron & Evans, L.L.P.

(57) ABSTRACT

Systems and methods of supplementing blood flow from the heart of a patient involving superficial, non-invasive procedures. In one general method, a first conduit is directed into the left side of the heart, a second conduit is directed into a superficial vessel and a pump is connected between the first and second conduits. The pump is implanted superficially in the patient and a power supply is connected to the pump. Blood is then suctioned from the left side of the patient's heart through the first conduit into the pump and expelled from the pump into the second conduit and the superficial vessel. A transcutaneous power supply is disclosed in one aspect and includes an external portion with a connection and alignment feature to assure reliable transmission of power.

20 Claims, 4 Drawing Sheets

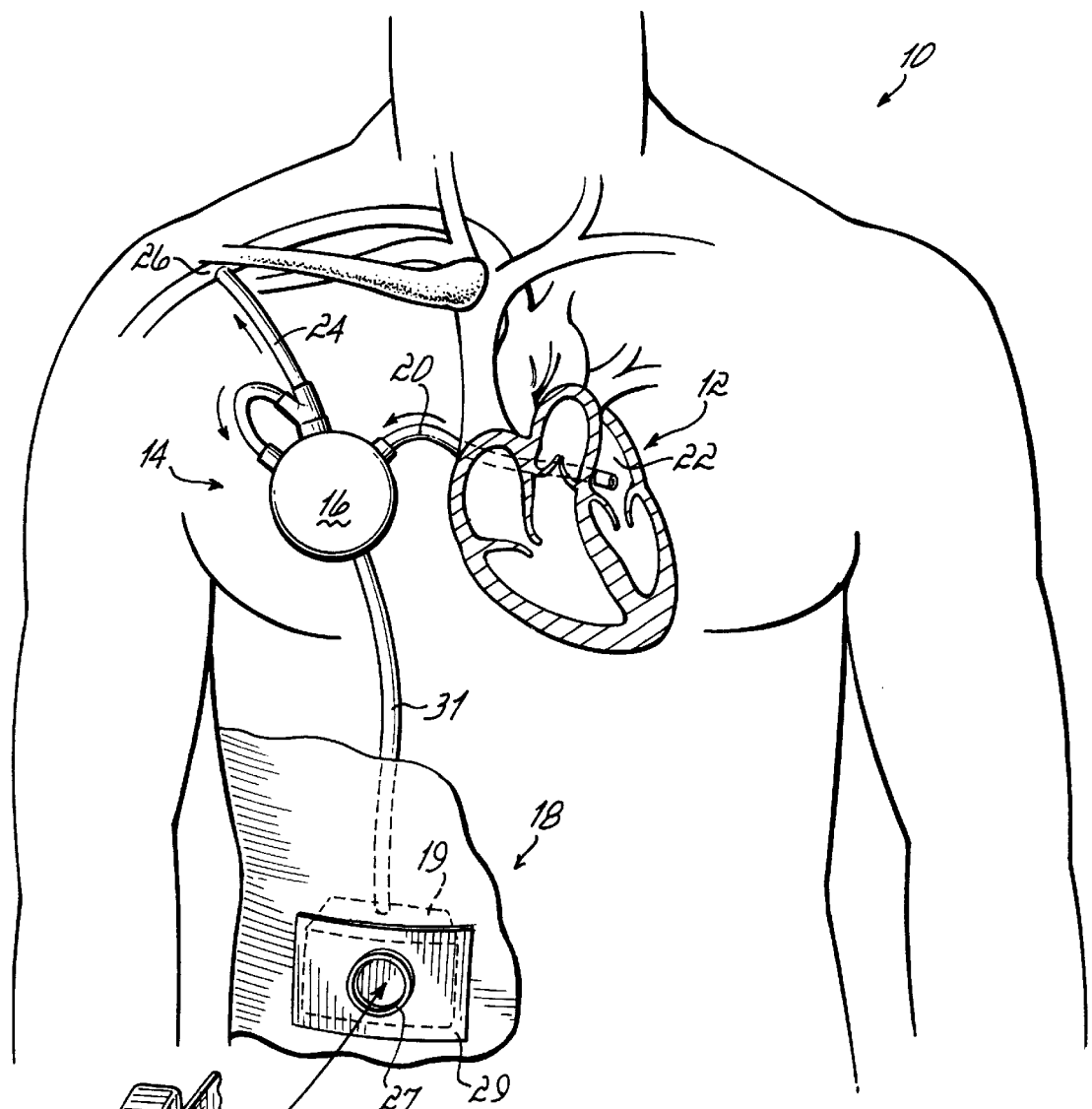
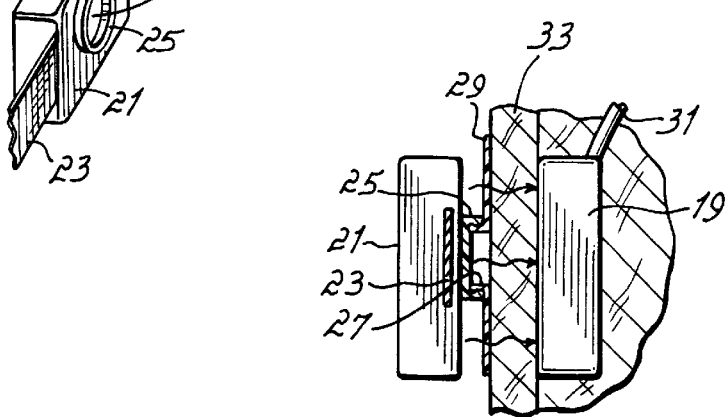
FIG. 1
FIG. 1A

SUPPLEMENTAL HEART PUMP METHODS AND SYSTEMS FOR SUPPLEMENTING BLOOD THROUGH THE HEART

FIELD OF THE INVENTION

The present invention generally relates to devices and methods for assisting heart function and, more particularly, devices and methods intended to supplement the natural blood pumping ability of a patient's native heart.

BACKGROUND OF THE INVENTION

Two major options exist for treating a weakened or diseased heart. A totally artificial heart may be implanted or a heart transplant may be performed, or a heart assist device may be used to supplement the function of the patient's natural heart to achieve a total blood flow through the heart which is acceptable. Most of the development in this area has been directed toward completely implantable heart replacements and significantly invasive heart assist devices which are bulky and complicated. There will always be some need for such devices, however, for every patient on the transplant list who may need a totally artificial heart there are fifty less serious cases of congestive heart failure in which the patient survives on other medical therapy. Unfortunately, the conventional medical therapies may not be sufficient to provide a high quality of life for the patient. Completely artificial hearts are also risky due to biological compatibility problems, blood clotting, manufacturing problems and regulatory issues. The surgical operation to install artificial hearts is very complex and, after installation, significant maintenance and follow-up is necessary.

Many patients will succeed with a partial heart assist which increases cardiac output by 20% to 50%. Such a device would well serve patients with idiopathic cardiomyopathy, ischemic cardiomyopathy, ischemic mitral regurgitation and progressive mitral regurgitation. In fact, a partial heart assist device may be completely sufficient for many potential transplant patients. Early installation of a partial heart assist device could unload the heart and prevent the development of congestive heart failure in patients with declining left ventricular function. If the hearts of these patients are partially unloaded with a suitable device, this could entirely avoid the need for surgery. Other patients may be too old for invasive surgery, but could lead higher quality lives with a suitable partial heart assist device. In all patients, aortic and mitral insufficiency (that is, volume overload conditions) are well-tolerated for many years until the heart begins to dilate. It may be desirable to allow these valves to leak to some extent, while unloading the heart and preventing dilation and the need for future surgery.

A large number of patients with ischemic coronary artery disease continue to have pain when they are undergoing maximal drug therapy. This maximal therapy is defined as the point when heart failure symptoms occur. With a suitable heart assist device, drug doses may be increased further while supporting the patient's heart with a partial heart assist device. Unloading dilated hearts with a partial or supplemental heart assist device may also reduce the risk of fatal arrhythmia and may be an effective adjunct for patients with defibrillators. It may also increase the amount of drug that can be effectively administered for arrhythmia as many of these agents depress contractility. Partial heart assist devices may also be useful after massive infarction to unload the heart and prevent unfavorable remodeling.

Ever since its introduction, the pacemaker has been widely accepted and very successful. The pacemaker is relatively simple to insert and does not require a major surgical operation. It is located superficially in a subcutaneous area of the patient's chest and is not regarded as highly invasive. As the market for pacemakers has grown, additional features have been added, such as defibrillators and cardioverters. Due to their simplicity and reliability, pacemakers are now inserted for even a suspicion of a potentially dangerous arrhythmia.

It would be desirable to provide a partial assist device or system along with associated methods which provide effective assistance with cardiac output as well as simplicity of design, ease of implantation, low cost and reliability. In essence, it would be desirable to provide a system and methods which combine the intentions of past heart assist devices with the simplicity, reliability, minimal invasiveness and other desirable attributes of a pacemaker-type device. A partial assist device which is only slightly more complex to insert than a pacemaker and that is as reliable, cost effective and as versatile as a pacemaker would increase the quality of life for many additional patients.

SUMMARY OF THE INVENTION

In one aspect, therefore, the present invention contemplates a device requiring only a small pocket made subcutaneously over the patient's chest, such as in the subclavicular region, as in a pacemaker, for housing a blood pump. Preferably, the size, shape and implant location would be similar to a pacemaker. The inflow for the pump is provided by a catheter or other conduit which is inserted into the left side of the heart, such as the left atrium, either by a small thoracotomy, sternotomy or by an endoscopic approach using ports placed in the chest. The cannula will then be passed out of the chest between the ribs and attached to the pump. The outflow from the pump may be completed by sewing a graft from the pump outlet to an artery in the shoulder area, such as an axillary artery, or by connecting a cannula between the pump and the shoulder artery. In short, oxygenated blood will be pumped from the left atrium of the heart to the shoulder artery and into the aorta. Various manners of powering the pump may be provided, such as by using a transcutaneous power supply with internal and external power coils, as known in the medical art, or other power supply either within the patient's body or outside the patient's body. An external energy source may be connected to the patient by a harness or belt. As another aspect of the invention, a reliable connection and alignment system is provided for the external portion of the power supply.

In a second aspect of the invention, the goal is to eliminate the intrathoracic part of the procedure. In this operation, the inflow cannula will pass from the axillary vein down the subclavian vein into the right atrium of the heart and across the septum in the left atrium. Blood will be withdrawn from the left atrium retrograde, up the subclavian vein inside the cannula and pumped into the axillary artery or another shoulder artery. The entire procedure may be accomplished from the same subclavicular incision. To augment blood flow, additional drainage catheters may be added from the opposite side of the chest or from the ipsilateral or contralateral neck veins. To simplify this procedure so that maximal blood flow is achieved, it may be easier to provide a large left atrial drainage cannula that occludes the right or left subclavian vein. In this case, however, the patient's arm may swell if the patient is not provided with a manner of returning blood from the arm. For this purpose, a second cannula, or a separate portion or orifice of the inflow cannula, may be used to pump the venous return from the arm around the obstruction and into the right side of the heart. As another alternative, the blue blood, or venous return from the arm may be mixed with the red blood or oxygenated blood from the left side of the heart and this mixture may be pumped back into the axillary artery. Provided that the left atrial blood is fully saturated, up to 25% venous blood could be mixed with the oxygenated blood or red blood from the left atrium before desaturation occurs.

Each of the procedures performed with products of the invention would require only a small incision in the shoulder area comparable to the size of a pacemaker or defibrillator. A pocket would be made for the pump and, for example, another pocket for a power coil or internal portion of a transcutaneous power supply. The subclavian vein would be cannulated for access to the left atrium of the heart and the outflow of the pump would be connected for fluid communication with the axillary artery or another shoulder artery. All of these portions of the procedure may be accessed through the same incision.

Various additional possibilities for the system and methods of this invention exist, including: 1) the cannulation points may vary, such as by making the artery or vein cannulation points anywhere in the shoulder or neck area, and not specifically in the subclavian vein and axillary artery; 2) when the left atrium is cannulated, the cannula will likely pass between the ribs, however, the cannula could also pass below the ribs, such as through the diaphragm, or above the ribs, such as out the thoracic inlet; 3) the left ventricle may be cannulated instead of the left atrium as a source of oxygenated blood; 4) the pump may be located inside or outside the chest or abdomen and not necessarily in a subcutaneous pocket on the outside of the chest or abdomen; 5) the pump may be implanted in the groin area of the patient and may draw blood from the left atrium or ventricle and return it to the groin area arteries either to the femoral arteries or via a retroperitoneal incision to the illiac arteries; 6) the pump may be located in a tube or in a separate unit and may be of any type and shape; 7) preferably run continuously and in a highly energy efficient manner; and 8) to shut down the system, a cannula associated with the device may be clamped or partly or entirely removed from the patient.

Additional modifications, substitutions, features and advantages of the invention will become more readily apparent to those of ordinary skill in the art upon review of the following detailed description of the presently preferred embodiments in conjunction with the the accompanying drawings.

BRIEF DESCRIPTION OF THE DRAWINGS

FIG. 1 is a schematic view of a patient with a supplemental heart pump device installed to pump blood from the left atrium to a shoulder artery.

FIG. 1A is an assembled, partial cross-section showing the power supply illustrated in exploded form in FIG. 1.

DETAILED DESCRIPTION OF THE PREFERRED EMBODIMENTS

Figure 2:
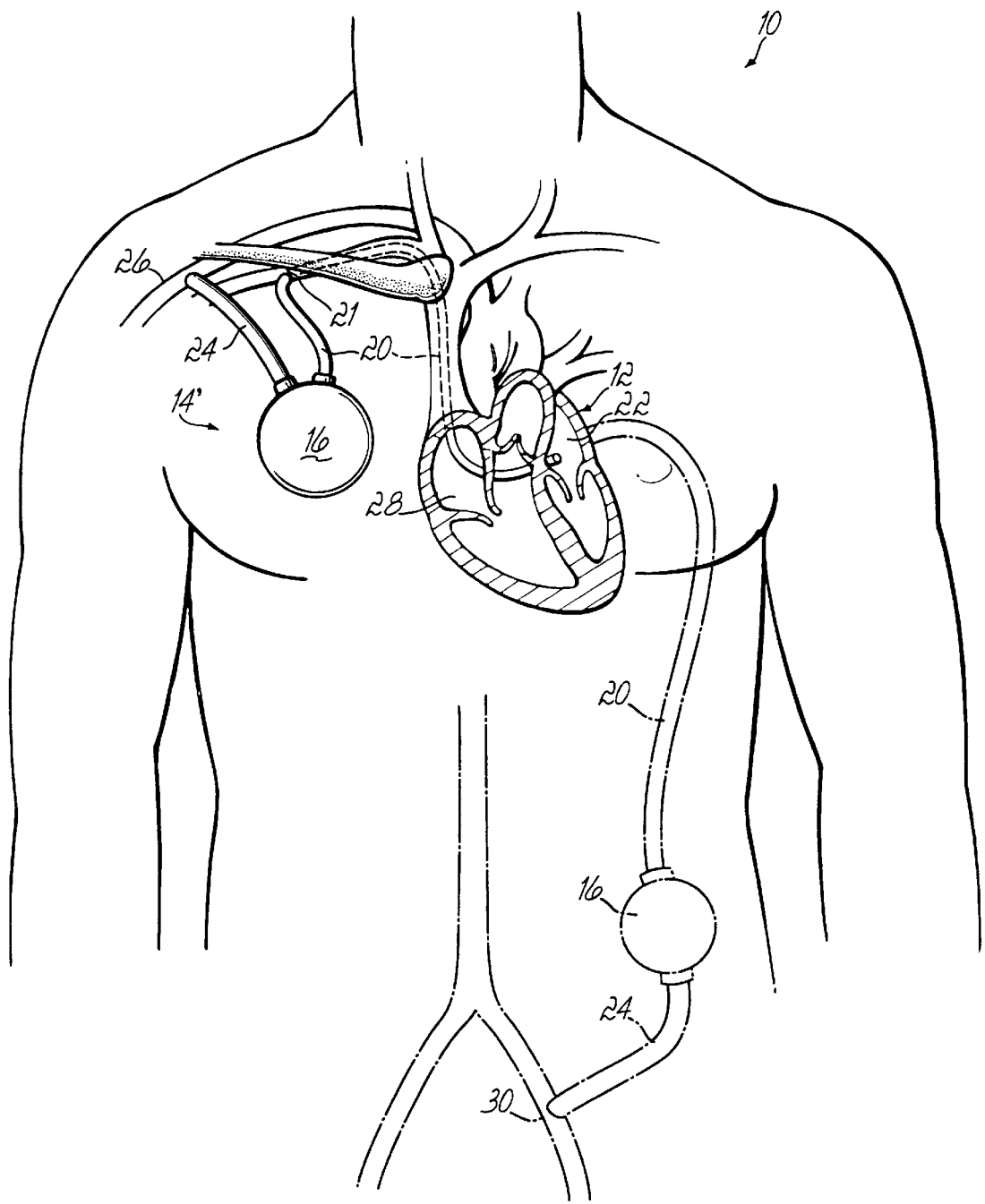
FIG. 2 is a schematic illustration similar to FIG. 1, but illustrating an alternative configuration of a supplemental heart pump system.

FIG. 1 illustrates a patient 10 having a heart 12, shown in longitudinal cross section, coupled with a supplemental assist device or system 14. System 14 comprises a pump 16 which may be implanted in a small pocket made subcutaneously over the patient's chest, such as in the subclavicular region as shown in the drawing. This is a similar implantation procedure to conventional pacemakers. Pump 1 6 is coupled with a control 17 and a suitable electric power supply 18. Pump 16 and control 17 may be constructed in various manners known in the art, for example, as a centrifugal pump or a screw type pump. Some more specific types of pumps are disclosed in U.S. Pat. Nos. 5,344,443; 5,941,813; and 5,947,892. Pump 16 may reside directly within one of the cannulas or conduits of system 14. Power supply 18 may be an implanted power supply or a power supply partially or wholly external to the patient. One particularly desirable power system comprises a transcutaneous power supply using a power coil which is periodically charged from outside the body to continuously operate pump 16. This system is discussed further below. Pump 16 is coupled with an inflow catheter 20 which extends through the heart, such as through the right atrium and septum, and into the left atrium 22. Blood is withdrawn from the left atrium 22 by pump 16 and discharged into catheter or conduit 24 which is connected for fluid communication with an artery in the shoulder region, such as axillary artery 26. As further illustrated in FIGS. 1 and 1A, power supply 18 most preferably comprises a first coil or power supply portion 19 implanted within the body of patient 10, such as in the lower abdominal region, and a second coil or power supply portion 21 positioned outside the patient's body. Second coil 21 may be in the form of a pack carried on a belt 23 worn by patient 10. In accordance with another inventive aspect, second coil 21 includes a first alignment element 25 and a second alignment element 27 is carried by an adhesive pad 29 affixed to the skin of patient 10. As further shown in FIG. 1, a power lead 31 is connected between first coil 19 and pump 16 for supplying electrical power to operate pump 16. Periodically, electrical power is transferred between second coil 21 and first coil 19 such that first coil 19 can deliver stored electrical power to pump 16. As one example, such a system may take the form of the one disclosed in U.S. Pat. No. 5,704,891, the disclosure of which is fully incorporated herein by reference. Such systems may allow second coil 21 to be removed from the patient for a period of time, such as during physical activity.

FIG. 2 illustrates an alternative heart assist pump system 14' comprising a pump 16 and respective inflow and outflow catheters or conduits 20, 24 as in the embodiment shown in FIG. 1. In this embodiment, like reference numerals refer to like elements with the first embodiment. In this embodiment, however, catheter 20 is installed through the axillary vein 21 and is directed into the heart 12 through the right atrium and septum and again into the left atrium 22. Conduit or catheter 24 is again coupled for fluid communication with the axillary artery 26 as in the embodiment of FIG. 1. In both embodiments, blood is withdrawn from the right atrium through conduit 20 and discharged into a suitable artery, such as the axillary artery 26. As another alternative shown in FIG. 2, pump 16 may instead be coupled between left atrium 22 and an artery in the patient's lower body, such as a femoral artery 30.

Figure 3:
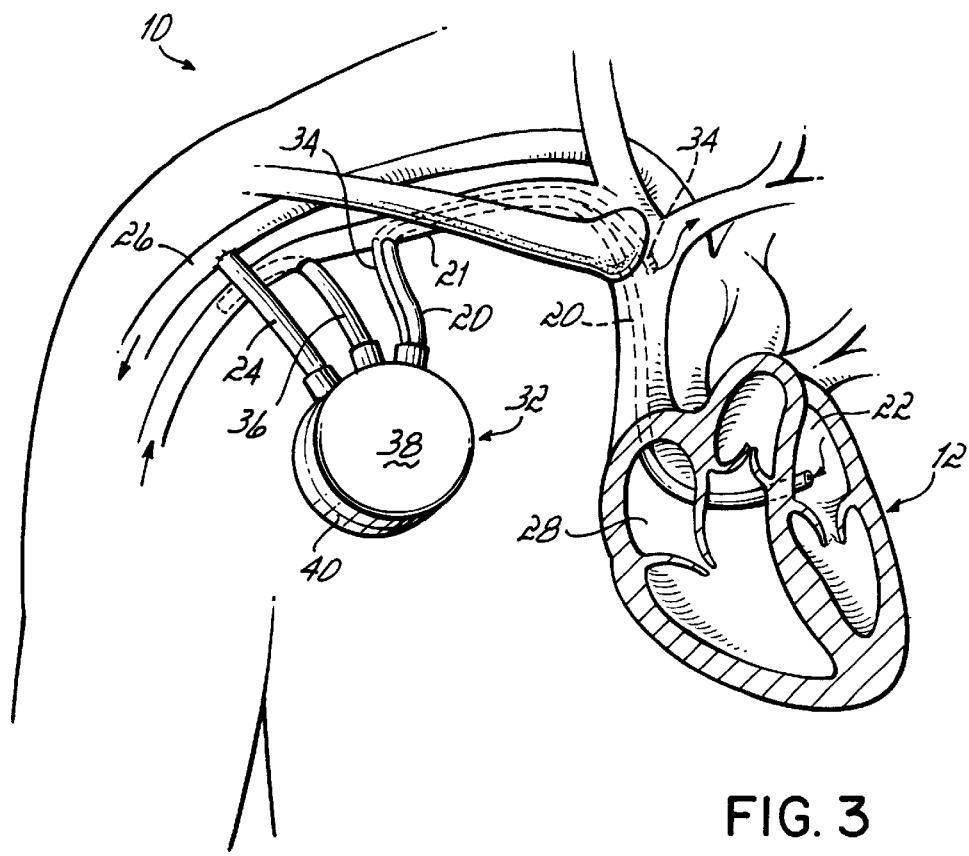
FIG. 3 is an enlarged view of the shoulder region of a patient showing another alternative supplemental heart pump system.

FIG. 3 illustrates another alternative heart assist device system 32 in which like reference numerals indicate like elements with FIGS. 1 and 2. In this embodiment, system 32 again includes conduits or catheters 20, 24 for respectively providing inflow and outflow of blood. This embodiment counteracts the potential obstruction created by conduit or catheter 20 in the axillary vein 21 by providing a separate set of conduits 34, 36. Specifically, in this embodiment a first pump 38 withdraws blood from the left atrium 22 through catheter or conduit 20 and discharges this blood through catheter or conduit 24 into axillary artery 26. A second pump 40, which may be superimposed on pump 38 in a pancake fashion as shown, withdraws blood from axillary vein 21 through conduit 36 and discharges this blood into conduit or catheter 34 to the right side of heart 12. This allows blood from the patient's arm to bypass the obstruction created by catheter or conduit 20 and therefore prevent any potential swelling problems of the patient's arm. It will be appreciated that the pumps associated with this invention may take many different forms including, but not limited to compact centrifugal pumps and peristaltic pumps.

Figure 4:
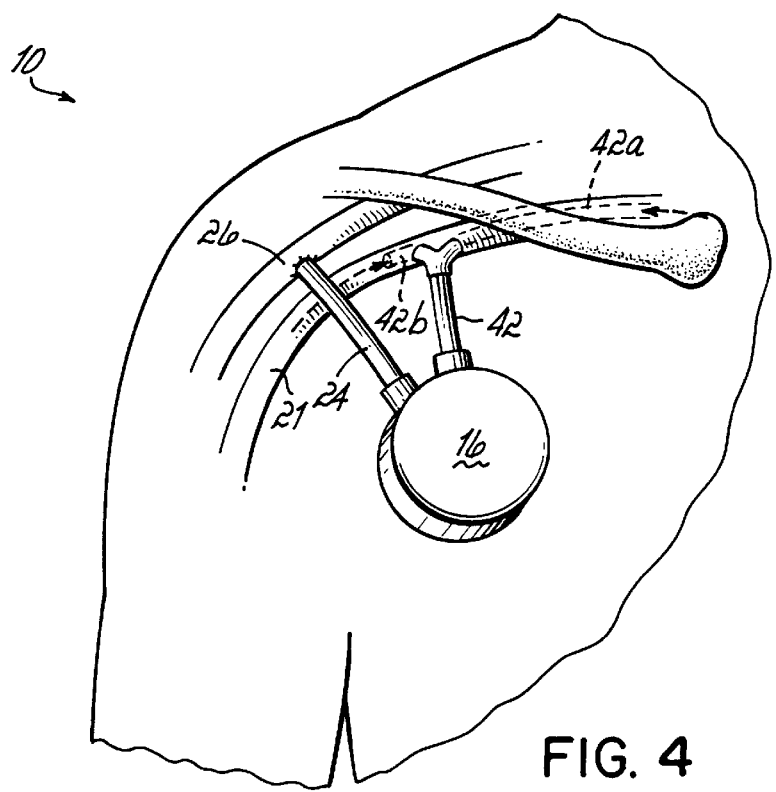
FIG. 4 is a fragmented view of the shoulder region of the patient illustrating another alternative supplemental heart pump system.

FIG. 4 illustrates another alternative solution to the obstruction problem referred to above. In this embodiment, pump 16 includes a conduit or catheter 24 which again provides outflow of blood to axillary artery 26. However, in this embodiment the inflow catheter or conduit 42 is connected to both the left side of the heart (not shown) through a catheter segment or branch 42a and also fluidly coupled to an opposite side of the axillary vein 21, for example, through a second catheter portion or branch 42b. This second catheter branch 42b may comprise an orifice in branch 42a. Here, the intention is to mix the blue blood or nonoxygenated blood returning from the patient's arm through axillary vein 21 and catheter branch 42b with the red blood or oxygenated blood being withdrawn from the left side of the patient's heart (not shown). Up to 25% of the venous blood or nonoxygenated blood may be mixed with the red blood before desaturation occurs. In this embodiment, the mixture of blood travels through conduit or catheter 42 and into pump 16 before being discharged through conduit or catheter 24 into axillary artery 26.

Figure 5:
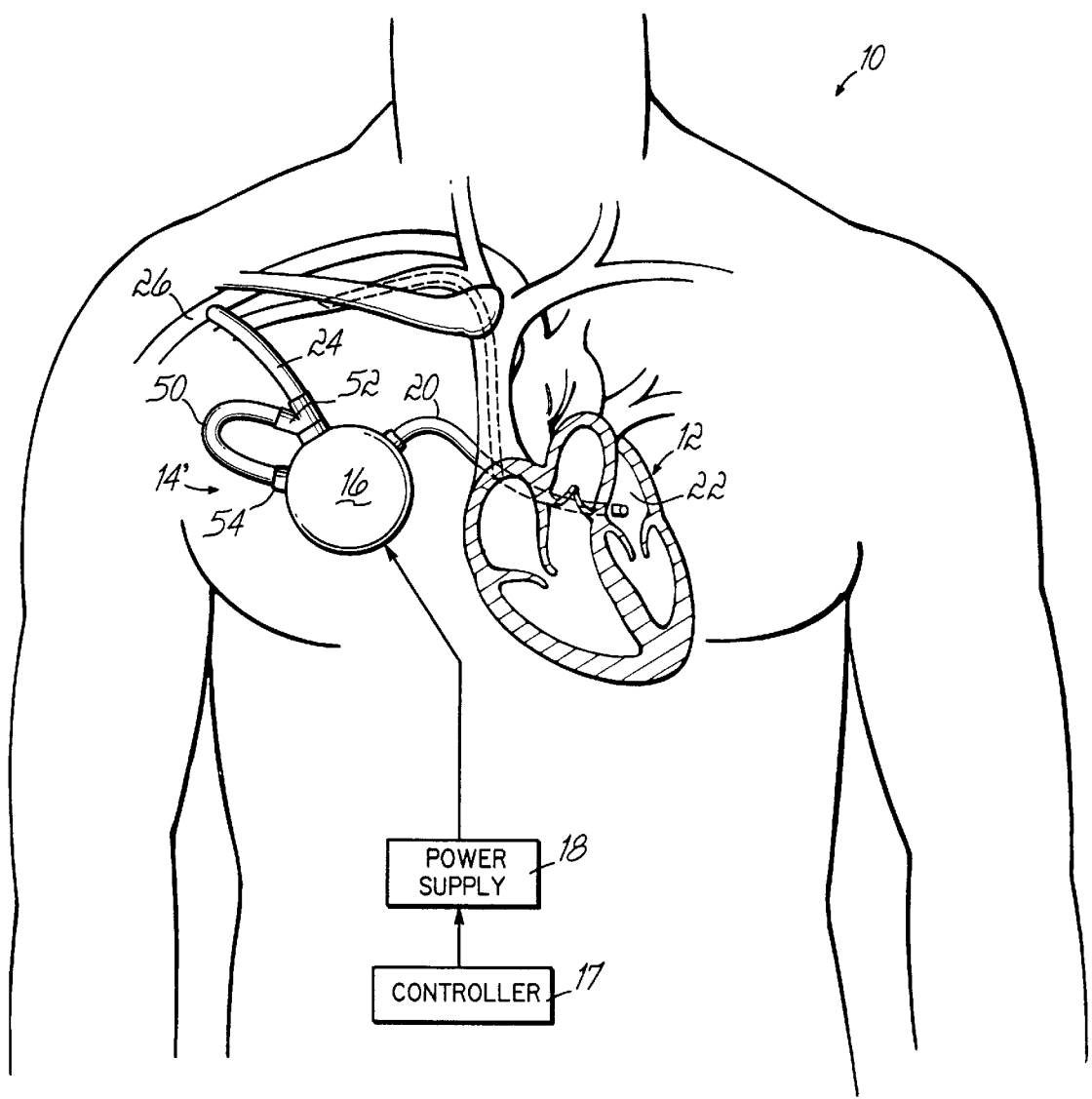
FIG. 5 is a schematic view of a patient with another alternative supplemental heart pump system.

FIG. 5 illustrates a system similar to the system shown in FIG. 1 with like reference numerals indicating like elements between the two embodiments. Power supply 18 may be the transcutaneous power supply illustrated in FIG. 1, or another transcutaneous system, fully implanted power supply system, or fully external power supply system. The only other difference between these two embodiments, as illustrated in FIG. 5, is the provision of a return conduit 50 coupled with system 14'. Return conduit 50 may lead to various locations of the system to provide a cleansing or rinsing function. For example, as there may be pumps 16 which include stagnant interior portions susceptible to accumulating blood clots, return conduit 50 is provided between an output 52 of pump 16 and an input 54 coupled with a suction side of pump 16 for returning a small portion of the blood output to the pump and, more particularly, to any portion or portions of the interior of pump which may be susceptible to stagnation and blood clot formation. Different pump configurations will have different areas of potential stagnation and these areas may be determined by those of ordinary skill in the art depending on the particular internal pump configuration. It is anticipated that return conduit 50 will preferably be sized and coupled with pump 16 such that only 5–10% of the blood output will be returned to pump 16 for this rinsing or cleaning function of any stagnant internal pump area. As necessitated by the particular pump system, additional return outputs may be provided depending on the number of system areas necessitating this function. One other example for the use of a return conduit in system 14' would be to lead a return conduit into the left atrium 22 to rinse an outside or inside end portion of conduit or catheter 20 to prevent clogging at this location.

While the present invention has been illustrated by a description of preferred embodiments and while these embodiments have been described in some detail, it is not the intention of the Applicant to restrict or in any way limit the scope of the appended claims to such detail. Additional advantages and modifications will readily appear to those skilled in the art. The various features and concepts of the invention may be used alone or in numerous combinations depending on the needs and preferences of the user. As one example, one or more conduits may be integrated into a single conduit structure having multiple flow paths. This has been a description of the present invention, along with the preferred methods of practicing the present invention as currently known. However, the invention itself should only be defined by the appended claims, wherein

I claim:

1. A method of supplementing the blood flow from the heart of a patient using a pump assist system, the method comprising:

directing a first conduit into the left side of the heart, coupling a second conduit in fluid communication with a superficial artery of the patient, connecting a pump between the first and second conduits, implanting the pump in a superficial, subcutaneous area of the patient, connecting an electrical power supply to the pump, suctioning blood from the left side of the heart through the first conduit and into the pump, and expelling the blood from the pump into the second conduit and the superficial artery.

2. The method of claim 1, wherein the step of directing a first conduit into the left side of the heart further comprises:

directing the first conduit into a superficial vein and transeptally through the heart.

3. The method of claim 2, wherein the first conduit includes first and second branches with the first branch communicating with the left side of the heart and the second branch fluidly communicating with the superficial vein, and the suctioning step further comprises suctioning blood from the left side of the heart through the first branch and suctioning blood from the superficial vein through the second branch, and the expelling step further comprises expelling the blood from the first and second branches into the second conduit.

4. The method of claim 1, wherein the step of implanting the pump further comprises:

implanting the pump superficially and subcutaneously in the chest region of the patient.

5. The method of claim 1, wherein the step of connecting a power supply further comprises:

connecting a transcutaneous power supply by implanting a first portion of said power supply superficially and subcutaneously in the patient and removably coupling a second portion of said supply outside the patient.

6. The method of claim 1, wherein the first conduit is introduced into the left side of the heart through the axillary vein of the patient.

7. The method of claim 6, further comprising:

directing a third conduit into the axillary vein, directing a fourth conduit into the axillary vein, and pumping blood from the third conduit to the fourth conduit and into the right side of the heart to bypass an obstruction formed by the first conduit.

8. The method of claim 1, wherein the second conduit is directed into the axillary artery of the patient.

9. The method of claim 1 further comprising:

returning a portion of the expelled blood to the pump before the portion of expelled blood reaches the superficial artery.

10. The method of claim 1 further comprising:

returning a portion of the expelled blood to another portion of the pump assist system and thereby performing a rinsing function.

11. A system for supplementing blood flow from the heart of a patient, the system comprising:

a first conduit configured to be directed transeptally into the left side of the heart, a second conduit configured to be coupled for fluid communication with a superficial artery of the patient, a third conduit, a fourth conduit, a pump configured to be superficially implanted within the patient and connected with the first and second conduits to suction blood from the first conduit and expel blood into the second conduit, and a second pump connected with the first pump and operatively coupled to the third and fourth conduits for suctioning blood from the third conduit and expelling the blood into the fourth conduit.

12. A system for supplementing blood flow from the heart of a patient, the system comprising:

a first conduit configured to be directed into the left side of the heart, a second conduit configured to be coupled for fluid communication with an artery of the patient, a pump configured to be implanted within the patient and connected with the first and second conduits to suction blood from the first conduit and expel blood into the second conduit, and a return conduit coupled with an outlet of said pump and another portion of said system for returning a portion of blood expelled by said pump from the return conduit to said other portion of said system.

13. A method of supplementing the blood flow from the heart of a patient using a pump assist system, the method comprising:

directing a first conduit into the left side of the heart, coupling a second conduit in fluid communication with a superficial artery of the patient, connecting a pump between the first and second conduits, implanting the pump in a superficial, subcutaneous chest region of the patient, suctioning blood from the left side of the heart through the first conduit and into the pump, and expelling the blood from the pump into the second conduit and the superficial artery.

14. The method of claim 13, wherein the step of directing a first conduit into the left side of the heart further comprises:

directing the first conduit into a superficial vein and transeptally through the heart.

15. The method of claim 14, wherein the first conduit includes first and second branches with the first branch communicating with the left side of the heart and the second branch fluidly communicating with the superficial vein, and the suctioning step further comprises suctioning blood from the left side of the heart through the first branch and suctioning blood from the superficial vein through the second branch, and the expelling step further comprises expelling the blood from the first and second branches into the second conduit.

16. The method of claim 13, wherein the second conduit is directed into the axillary artery of the patient.

17. The method of claim 13 further comprising:

returning a portion of the expelled blood to the pump before the portion of expelled blood reaches the superficial artery.

18. The method of claim 13 further comprising:

returning a portion of the expelled blood to another portion of the pump assist system to perform a rinsing function.

19. The method of claim 13, wherein the first conduit is introduced into the left side of the heart through the axillary vein of the patient.

20. The method of claim 19, further comprising:

directing a third conduit into the axillary vein, directing a fourth conduit into the axillary vein, and pumping blood from the third conduit to the fourth conduit and into the right side of the heart to bypass an obstruction formed by the first conduit.

* * * * *

US006530876C1

(12) INTER PARTES REEXAMINATION CERTIFICATE (978th)

United States Patent
Spence

(10) Number: US 6,530,876 C1
(45) Certificate Issued: Oct. 27, 2014

(54) SUPPLEMENTAL HEART PUMP METHODS AND SYSTEMS FOR SUPPLEMENTING BLOOD THROUGH THE HEART

(75) Inventor: Paul A. Spence, Louisville, KY (US)

(73) Assignee: Heartware, Inc., Framingham, MA (US)

Reexamination Request:
No. 95/001,858, Dec. 19, 2011

Reexamination Certificate for:
Patent No.: 6,530,876
Issued: Mar. 11, 2003
Appl. No.: 09/557,562
Filed: Apr. 25, 2000

(51) Int. Cl.
*A61N 1/362* (2006.01)
(52) U.S. Cl.
USPC ............................................. 600/16
(58) Field of Classification Search
USPC .......................................... 607/27
See application file for complete search history.

(56) References Cited

To view the complete listing of prior art documents cited during the proceeding for Reexamination Control Number 95/001,858, please refer to the USPTO's public Patent Application Information Retrieval (PAIR) system under the Display References tab.

*Primary Examiner* — Beverly M. Flanagan

(57) ABSTRACT

Systems and methods of supplementing blood flow from the heart of a patient involving superficial, non-invasive procedures. In one general method, a first conduit is directed into the left side of the heart, a second conduit is directed into a superficial vessel and a pump is connected between the first and second conduits. The pump is implanted superficially in the patient and a power supply is connected to the pump. Blood is then suctioned from the left side of the patient's heart through the first conduit into the pump and expelled from the pump into the second conduit and the superficial vessel. A transcutaneous power supply is disclosed in one aspect and includes an external portion with a connection and alignment feature to assure reliable transmission of power.

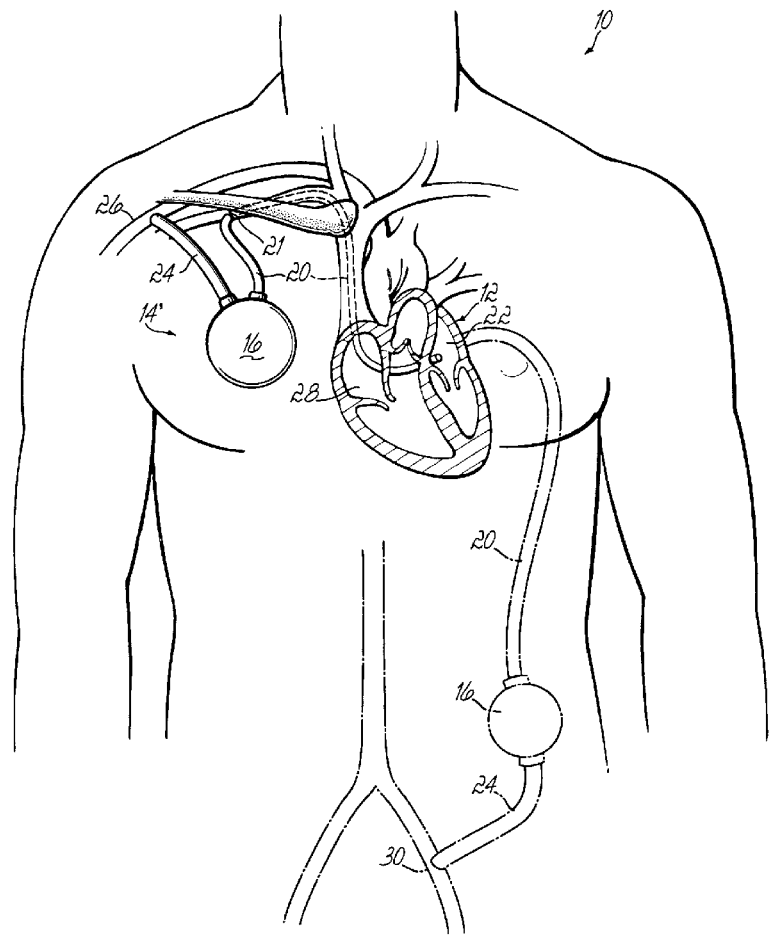

US 6,530,876 C1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 5, 8, 13, 14 and 16 are cancelled.

New claims 21-62 are added and determined to be patentable.

Claims 3, 6, 7, 9-12, 15 and 17-20 were not reexamined.

*21. The method of claim 1, wherein the implanting the pump includes implanting the pump in a subclavicular region of the patient.*

*22. The method of claim 13, wherein the implanting the pump includes implanting the pump in a subclavicular region of the patient.*

*23. The method of claim 2, wherein the implanting the pump includes implanting the pump in a subclavicular region of the patient.*

*24. The method of claim 14, wherein the implanting the pump includes implanting the pump in a subclavicular region of the patient.*

*25. The method of claim 8, wherein the implanting the pump includes implanting the pump in a subclavicular region of the patient.*

*26. The method of claim 16, wherein the implanting the pump includes implanting the pump in a subclavicular region of the patient.*

*27. The method of claim 1, wherein the directing the first conduit includes directing a first end portion of the first conduit into the left side of the heart and a second end portion of the first conduit to a pocket formed in a subclavicular region of the patient.*

*28. The method of claim 13, wherein the directing the first conduit includes directing a first end portion of the first conduit into the left side of the heart and a second end portion of the first conduit to a pocket formed in a subclavicular region of the patient.*

*29. The method of claim 2, wherein the directing the first conduit includes directing a first end portion of the first conduit into the left side of the heart and a second end portion of the first conduit to a pocket formed in a subclavicular region of the patient.*

*30. The method of claim 14, wherein the directing the first conduit includes directing a first end portion of the first conduit into the left side of the heart and a second end portion of the first conduit to a pocket formed in a subclavicular region of the patient.*

*31. The method of claim 8, wherein the directing the first conduit includes directing a first end portion of the first conduit into the left side of the heart and a second end portion of the first conduit to a pocket formed in a subclavicular region of the patient.*

*32. The method of claim 16, wherein the directing the first conduit includes directing a first end portion of the first conduit into the left side of the heart and a second end portion of the first conduit to a pocket formed in a subclavicular region of the patient.*

*33. The method of claim 1, wherein the directing the first conduit includes cannulating a vein in one of a shoulder area or a neck area and directing an end portion of the first conduit through the right atrium and the septum and into the left atrium.*

*34. The method of claim 13, wherein the directing the first conduit includes cannulating a vein in one of a shoulder area or a neck area and directing an end portion of the first conduit through the right atrium and the septum and into the left atrium.*

*35. The method of claim 2, wherein the directing the first conduit includes cannulating the superficial vein in one of a shoulder area or a neck area and directing an end portion of the first conduit through the right atrium and the septum and into the left atrium.*

*36. The method of claim 14, wherein the directing the first conduit includes cannulating the superficial vein in one of a shoulder area or a neck area and directing an end portion of the first conduit through the right atrium and the septum and into the left atrium.*

*37. The method of claim 8, wherein the directing the first conduit includes cannulating a vein in one of a shoulder area or a neck area and directing an end portion of the first conduit through the right atrium and the septum and into the left atrium.*

*38. The method of claim 16, wherein the directing the first conduit includes cannulating a vein in one of a shoulder area or a neck area and directing an end portion of the first conduit through the right atrium and the septum and into the left atrium.*

*39. The method of claim 1, further comprising passing an end portion of the first conduit out of the chest of the patient between the ribs of the patient.*

*40. The method of claim 21, further comprising passing an end portion of the first conduit out of the chest of the patient between the ribs of the patient.*

*41. The method of claim 23, further comprising passing an end portion of the first conduit out of the chest of the patient between the ribs of the patient.*

*42. The method of claim 25, further comprising passing an end portion of the first conduit out of the chest of the patient between the ribs of the patient.*

*43. The method of claim 13, further comprising an end portion of the first conduit out of the chest of the patient between the ribs of the patient.*

*44. The method of claim 22, further comprising passing an end portion of the first conduit out of the chest of the patient between the ribs of the patient.*

*45. The method of claim 24, further comprising passing an end portion of the first conduit out of the chest of the patient between the ribs of the patient.*

*46. The method of claim 26, further comprising passing an end portion of the first conduit out of the chest of the patient between the ribs of the patient.*

*47. The method of claim 1, wherein the directing the first conduit, the coupling the second conduit, and the implanting the pump are accomplished from a subclavicular incision.*

*48. The method of claim 13, wherein the directing the first conduit, the coupling the second conduit, and the implanting the pump are accomplished from a subclavicular incision.*

*49. The method of claim 47, wherein a size of the subclavicular incision is comparable to any one of a size of a pacemaker or a size of a defibrillator.*

50. The method of claim 48, wherein a size of the subclavicular incision is comparable to any one of a size of a pacemaker or a size of a defibrillator.

51. The method of claim 2, wherein the directing the first conduit into the superficial vein includes cannulating a vein at a cannulating point in one of a shoulder area or a neck area of the patient.

52. The method of claim 14, wherein the directing the first conduit into the superficial vein includes cannulating a vein at a cannulation point in one of a shoulder or a neck area of the patient.

53. The method of claim 1, wherein the directing the first conduit includes passing the first conduit beneath the body of a clavicle of the patient.

54. The method of claim 2, wherein the directing the first conduit includes passing the first conduit beneath the body of a clavicle of the patient.

55. The method of claim 8, wherein the directing the first conduit includes passing the first conduit beneath the body of a clavicle of the patient.

56. The method of claim 51, wherein the directing the first conduit includes passing the first conduit beneath the body of a clavicle of the patient.

57. The method of claim 13, wherein the directing the first conduit includes passing the first conduit beneath the body of a clavicle of the patient.

58. The method of claim 14, wherein the directing the first conduit includes passing the first conduit beneath the body of a clavicle of the patient.

59. The method of claim 16, wherein the directing the first conduit includes passing the first conduit beneath the body of a clavicle of the patient.

60. The method of claim 52, wherein the directing the first conduit includes passing the first conduit beneath the body of a clavicle of the patient 61. The method of claim 1 wherein:
the coupling the second conduit includes directing the second conduit into an artery in a shoulder region of the patient; and
the implanting the pump includes implanting the pump in a subclavicular region of the patient.

62. The method of claim 13, wherein:
the coupling the second conduit includes directing the second conduit into an artery in a shoulder region of the patient; and
wherein the implanting the pump includes implanting the pump in a subclavicular region of the patient.

\* \* \* \* \*